US00PP22852P2

(12) United States Plant Patent
Vlielander

(10) Patent No.: US PP22,852 P2
(45) Date of Patent: Jul. 10, 2012

(54) ***KALANCHOE* PLANT NAMED 'FICALANJAMAICA'**

(50) Latin Name: *Kalanchoe blossfeldiana*
Varietal Denomination: Ficalanjamaica

(75) Inventor: Ike J. Vlielander, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 12/931,628

(22) Filed: Feb. 3, 2011

(51) Int. Cl.
*A01H 5/00* (2006.01)

(52) U.S. Cl. ..... Plt./338

(58) Field of Classification Search ..... Plt./338
See application file for complete search history.

(56) References Cited

OTHER PUBLICATIONS

Pluto Plant Variety database 2011/05. Search for Ficalanjamaica.*

* cited by examiner

*Primary Examiner* — Annette Para
(74) *Attorney, Agent, or Firm* — C. A. Whealy

(57) ABSTRACT

A new and distinct cultivar of *Kalanchoe* plant named 'Ficalanjamaica', characterized by its compact, upright and uniformly mounded plant habit; moderately vigorous growth habit; freely branching plant habit; glossy dark green-colored leaves; uniform and freely flowering habit; double bright yellow-colored flowers; and excellent postproduction longevity.

1 Drawing Sheet

Botanical designation: *Kalanchoe blossfeldiana.*
Cultivar denomination: 'FICALANJAMAICA'.

BACKGROUND OF THE INVENTION

The present invention relates to a new and distinct cultivar of *Kalanchoe* plant, botanically known as *Kalanchoe blossfeldiana* and hereinafter referred to by the name 'Ficalanjamaica'.

The new *Kalanchoe* is a product of a planned breeding program conducted by the Inventor in De Lier, The Netherlands. The objective of the breeding program is to create new freely-branching and freely-flowering *Kalanchoe* plants with double flowers and attractive foliage and flower coloration.

The new *Kalanchoe* plant originated from a cross-pollination made by the Inventor in Odense, Denmark in September, 2006 of a proprietary selection of *Kalanchoe blossfeldiana* identified as code number 1110 (05), not patented, as the female, or seed, parent with a proprietary selection of *Kalanchoe blossfeldiana* identified as code number 9185-02 (05), not patented, as the male, or pollen, parent. The new *Kalanchoe* plant was discovered and selected by the Inventor as a single flowering plant from within the progeny of the stated cross-pollination in a controlled environment in De Lier, The Netherlands.

Asexual reproduction of the new *Kalanchoe* plant by vegetative terminal cuttings in a controlled environment in De Lier, The Netherlands since 2008 has shown that the unique features of this new *Kalanchoe* plant are stable and reproduced true to type in successive generations.

SUMMARY OF THE INVENTION

Plants of the new *Kalanchoe* have not been observed under all possible environmental conditions and cultural practices. The phenotype may vary somewhat with variations in environmental conditions such as temperature, daylength and light intensity without, however, any variance in genotype.

The following traits have been repeatedly observed and are determined to be the unique characteristics of 'Ficalanjamaica'. These characteristics in combination distinguish 'Ficalanjamaica' as a new and distinct *Kalanchoe* plant:

1. Compact, upright and uniformly mounded plant habit.
2. Moderately vigorous growth habit.
3. Freely branching plant habit.
4. Glossy dark green-colored leaves.
5. Uniform and freely flowering habit.
6. Double bright yellow-colored flowers.
7. Excellent postproduction longevity.

Plants of the new *Kalanchoe* can be compared to plants of the female parent selection. Plants of the new *Kalanchoe* differ from plants of the female parent selection in the following characteristics:

1. Plants of the new *Kalanchoe* are more compact than plants of the female parent selection.
2. Plants of the new *Kalanchoe* are more freely branching than plants of the female parent selection.
3. Plants of the new *Kalanchoe* have smaller leaves than plants of the female parent selection.
4. Plants of the new *Kalanchoe* and the female parent selection differ in flower color as plants of the female parent selection have orange-colored flowers.

Plants of the new *Kalanchoe* can be compared to plants of the male parent selection. Plants of the new *Kalanchoe* differ from plants of the male parent selection in the following characteristics:

1. Plants of the new *Kalanchoe* have double flowers whereas plants of the male parent selection have single flowers.
2. Flowers of plants of the new *Kalanchoe* are brighter yellow in color than flowers of plants of the male parent selection.

Plants of the new *Kalanchoe* can be compared to plants of the *Kalanchoe blossfeldiana* 'Golden Girl', not patented. In side-by-side comparisons conducted in De Lier, The Netherlands, plants of the new *Kalanchoe* differed from plants of 'Golden Girl' in the following characteristics:

1. Plants of the new *Kalanchoe* were more compact than plants of 'Golden Girl'.
2. Plants of the new *Kalanchoe* were more freely branching than plants of 'Golden Girl'.
3. Plants of the new *Kalanchoe* had smaller leaves than plants of 'Golden Girl'.
4. Plants of the new *Kalanchoe* and 'Golden Girl' differed in flower color as plants of 'Golden Girl' had yellow orange-colored flowers.

BRIEF DESCRIPTION OF THE PHOTOGRAPH

The accompanying colored photograph illustrates the overall appearance of the new *Kalanchoe* plant showing the colors as true as it is reasonably possible to obtain in colored reproductions of this type. Colors in the photograph may differ slightly from the color values cited in the detailed botanical description which accurately describe the colors of the new *Kalanchoe* plant.

The photograph comprises a side perspective view of a typical flowering plant of 'Ficalanjamaica' grown in a container.

DETAILED BOTANICAL DESCRIPTION

The aforementioned photograph and following observations, measurements and values describe plants grown during the summer and autumn in 10-cm containers in a glass-covered greenhouse in De Lier, The Netherlands and under conditions which closely approximate commercial *Kalanchoe* production. During the production of the plants, day temperatures ranged from 20° C. to 22° C., night temperatures ranged from 19° C. to 21° C. and light levels ranged from 10,000 lux to 50,000 lux. Plants received long day/short night conditions (more than 14 hours of light) for about three weeks then plants received photoinductive short day/long night conditions (minimum 14 hours darkness) until flowering. Plants were 17 weeks old when the photograph and the description were taken. In the detailed description, color references are made to The Royal Horticultural Society Colour Chart, 2007 Edition, except where general terms of ordinary dictionary significance are used.

Botanical classification: *Kalanchoe blossfeldiana* 'Ficalanjamaica'.

Parentage:

*Female, or seed, parent*.—Proprietary selection of *Kalanchoe blossfeldiana* identified as code number 1110 (05), not patented.

*Male or pollen parent*.—Proprietary selection of *Kalanchoe blossfeldiana* identified as code number 9185-02 (05), not patented.

Propagation:

*Type*.—By vegetative terminal cuttings.

*Time to initiate roots, summer*.—About eleven days at temperatures of 21° C.

*Time to initiate roots, winter*.—About 16 days at temperatures of 21° C.

*Time to produce a rooted young plant, summer*.—About three weeks at temperatures of 21° C.

*Time to produce a rooted young plant, winter*.—About four weeks at temperatures of 21° C.

*Root description*.—Fine, fibrous; greyish white in color.

*Rooting habit*.—Freely branching; dense.

Plant description:

*Plant and growth habit*.—Compact, upright and uniformly mounded plant habit; freely flowering habit with numerous racemes positioned above the foliar plane; inverted triangle with rounded crown; appropriate for 10 to 15-cm containers; moderately vigorous growth habit.

*Plant height at flowering*.—About 16 cm.

*Plant diameter at flowering*.—About 17 cm.

*Branching habit*.—Freely branching, usually about five to eight lateral branches develop per plant; pinching (removal of the terminal apex) is not required but will enhance lateral branch development.

Lateral branch description:

*Length*.—About 10 cm to 13 cm.

*Diameter*.—About 2 mm to 4 mm.

*Internode length*.—About 2 cm to 4 cm.

*Aspect*.—Erect.

*Strength*.—Strong.

*Texture*.—Smooth, glabrous.

*Color*.—Close to 137B.

Foliage description:

*Arrangement*.—Opposite, simple; generally symmetrical; mostly flat; glossy.

*Quantity per plant*.—About 8 to 13 mature leaves and about 14 to 22 generative leaves.

*Length*.—About 10.5 cm.

*Width*.—About 8.5 cm.

*Shape*.—Ovate.

*Apex*.—Obtuse.

*Base*.—Obtuse.

*Margin*.—Crenate.

*Texture, upper and lower surfaces*.—Smooth, glabrous; coriaceous; succulent.

*Venation pattern*.—Pinnate.

*Color*.—Developing and fully developed leaves, upper surface: Close to 147A; venation, close to 147A. Developing and fully developed foliage, lower surface: Close to 146A; venation, close to 148A.

*Petiole*.—Length: About 1.2 cm. Diameter: About 4 mm to 8 mm. Texture, upper and lower surfaces: Smooth, glabrous. Color, upper and lower surfaces: Close to 138A.

Flower description:

*Flower arrangement and habit*.—Double flowers arranged singly in racemes that arise from leaf axils; uniform and freely flowering habit with usually about 25 open flowers and about 25 flower buds per lateral branch and more than 150 open flowers and flower buds per plant; flowering continuously for at least seven weeks.

*Fragrance*.—None detected.

*Natural flowering season*.—Plants of the new *Kalanchoe* initiate and develop flowers under short day/long night conditions or during November and December in The Netherlands; flower initiation and development can also be induced under artificial short day/long conditions (at least 14 hours of darkness).

*Time to flower*.—Under short day/long night photoinductive conditions, plants begin flowering in about ten to twelve weeks; actual time to flower is primarily dependent upon temperature and light intensity.

*Post-production longevity*.—Excellent post-production longevity; plants maintain good foliage and flower substance for about seven weeks under interior environmental conditions; individual flowers last about 20 days on the plant; flowers persistent.

*Flower diameter*.—About 1.8 cm.

*Flower length* (*height*).—About 1.4 cm.

*Flower bud*.—Shape: Initially oblong, becoming tubular ovoid with development. Length: About 1.3 cm. Diameter: About 4 mm. Color: Close to 4D and 14C.

*Petals*.—Arrangement: About 30 to 36 in whorls; petals imbricate. Length: About 6 mm to 8 mm. Width: About 3 mm to 5 mm. Aspect: Flat to partially upright. Shape: Ovate. Apex: Acute. Margin: Entire. Texture, upper and lower surfaces: Smooth, glabrous. Color: When opening, upper surface: Close to 14A. When opening, lower surface: Close to 14D. Fully opened, upper surface: Close to 14B; color becoming closer to 14C with development. Fully opened, lower surface: Close to 14D.

*Sepals*.—Appearance: Four in a single whorl. Length: About 8 mm. Width: About 1.5 mm. Shape: Oblong, pointed. Apex: Acute. Base: Obtuse. Margin: Entire. Aspect: Upright. Texture, upper and lower surfaces: Smooth; glabrous. Color, upper and lower surfaces: Close to 138B.

*Peduncles*.—Length: About 3 mm to 5 mm. Diameter: About 2 mm. Aspect: Erect. Strength: Strong. Texture: Smooth, glabrous. Color: Close to 138B.

*Reproductive organs*.—Androecium: Stamen number: None to eight per flower. Anther shape: Elliptic, flat. Anther length: About 0.3 mm. Anther color: Close to 150D. Amount of pollen: Scarce. Pollen color: Close to 12A. Gynoecium: Pistil number: About four to eight per flower. Pistil length: About 1 mm. Style length: About 1 mm. Style color: Close to 138D. Stigma shape: Flat. Stigma color: Close to 8D. Ovary color: Close to 138D.

*Seeds*.—Length: About 0.1 mm. Diameter: About 0.05 mm. Color: Close to 166C.

Temperature tolerance: Plants of the new *Kalanchoe* have been observed to tolerate temperatures from about 16° C. to about 35° C.

Pathogen/pest resistance: Plants of the new *Kalanchoe* have not been observed to be resistant to pests and pathogens common to *Kalanchoes*.

It is claimed:

1. A new and distinct *Kalanchoe* plant named 'Ficalanjamaica' as illustrated and described.

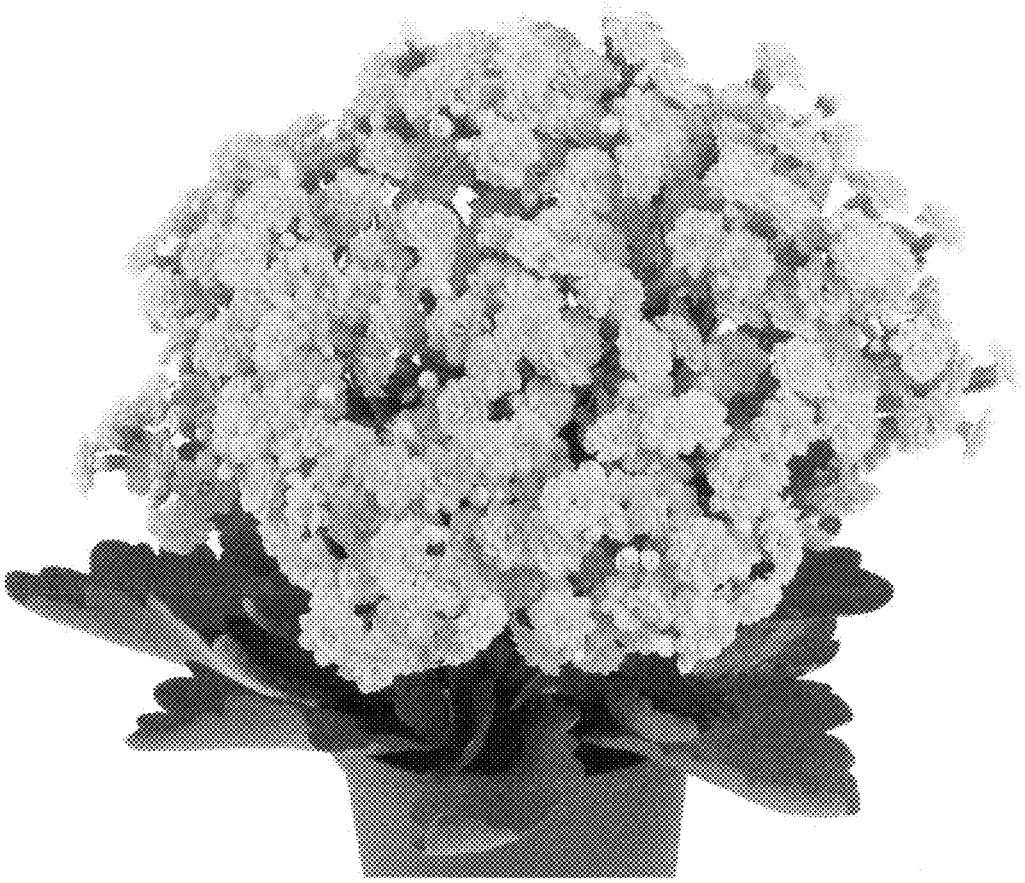

* * * * *